United States Patent [19]

Lindegren

[11] Patent Number: 5,713,943
[45] Date of Patent: Feb. 3, 1998

[54] ELECTRODE SYSTEM WITH A BIODEGRADABLE TUBE FOR RECEIVING A STYLET

[75] Inventor: Ulf Lindegren, Enskede, Sweden

[73] Assignee: Pacesetter AB, Solna, Sweden

[21] Appl. No.: 771,659

[22] Filed: Dec. 23, 1996

[30] Foreign Application Priority Data

Dec. 28, 1995 [SE] Sweden ................... 9504677-7

[51] Int. Cl.6 ........................................... A61N 1/05
[52] U.S. Cl. ...................... 607/116; 607/119; 128/642
[58] Field of Search .......................... 128/642; 607/115, 607/116, 117, 122

[56] References Cited

U.S. PATENT DOCUMENTS 4,136,703  1/1979  Wittkampf .
4,258,724  3/1981  Balat et al. .
5,480,420  1/1996  Hoegrelid et al. ............ 128/642
5,571,161  11/1996  Starksen ......................... 607/119

FOREIGN PATENT DOCUMENTS 0 085 967  8/1983  European Pat. Off. .
0 652 017  5/1995  European Pat. Off. .

*Primary Examiner*—William E. Kamm
*Assistant Examiner*—George R. Evanisko
*Attorney, Agent, or Firm*—Hill, Steadman & Simpson

[57] ABSTRACT

An electrode cable for implantation in a body cavity has a tube made of a biodegradable, biocompatible polymer material attached to the exterior of the cable, the tube forming a channel for a stylet.

6 Claims, 1 Drawing Sheet

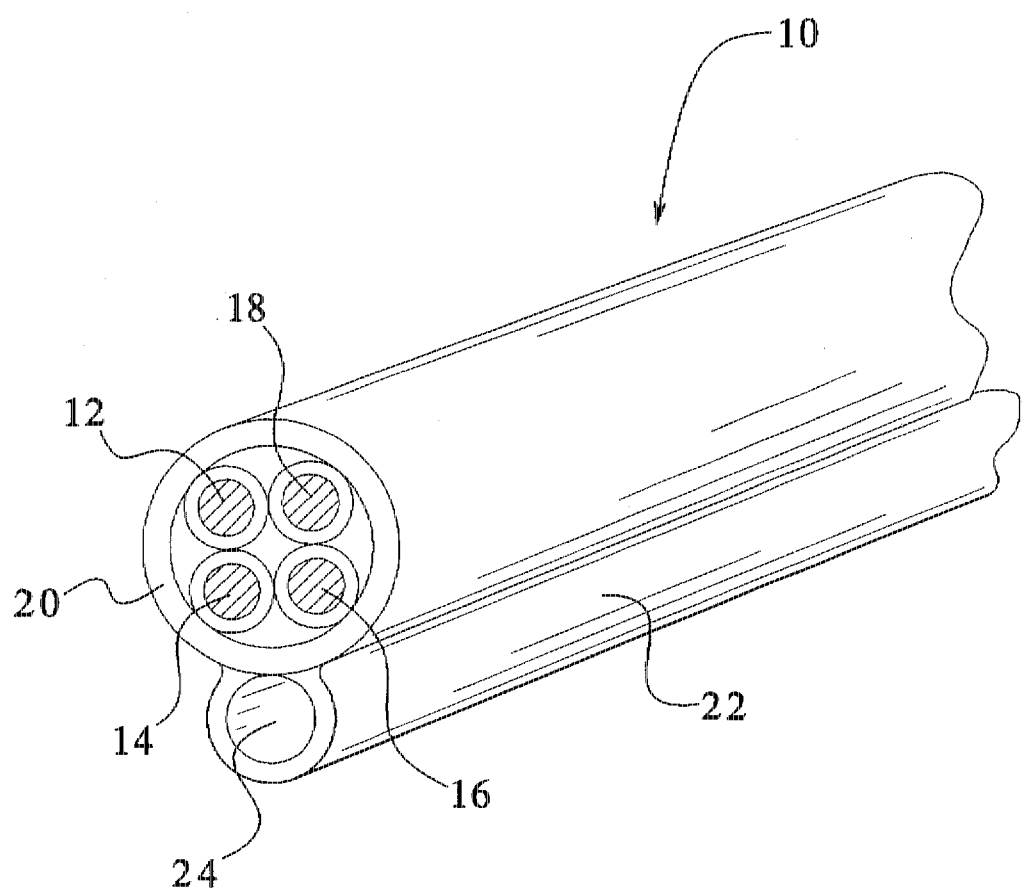

ELECTRODE SYSTEM WITH A BIODEGRADABLE TUBE FOR RECEIVING A STYLET

BACKGROUND OF THE INVENTION

1. Field of the Invention

The present invention relates to an electrode cable intended for implantation in a body cavity, particularly for intracardiac stimulation and/or sensing of heart signals, of the type having at least one elongate, flexible, electrical conductor with a distal end and a proximal end, an electrode arranged at the distal end of the conductor for fixing to tissue in a heart wall, and a channel for the insertion of a stiffening/guiding stylet for the conductor.

2. Description of the Prior Art

Known electrode cables of the above type in common use (see e.g. U.S. Pat. No. 4,136,703) normally have a central channel formed by one or more coaxially coiled, insulated electrical conductors, a stylet being intended for insertion into the channel during advancement of the electrode cable through e.g. a vein to the heart in order to stiffen the flexible cable and to guide the distal end of the electrode cable to the desired anchoring site in a ventricle or atrium of the heart. As a result of the tight helical coiling of the conductor or conductors and the presence of an external silicone rubber sleeve, the diameter of the electrode cable is relatively large (about 2 mm) in relation to the diameter of the individual conductors and the channel leaves, after implantation, an empty, superfluous central space in the cable.

SUMMARY OF THE INVENTION

An object of the present invention is to provide an electrode cable which, in the implanted state, is thinner and more pliant than known unipolar and bipolar electrode cables. Another object is to provide an electrode cable having a diameter comparable to a conventional electrode cable but which can contain a larger number of separate electrodes to form a relatively thin, multipolar electrode cable, which can still accommodate a stylet.

For this purpose, an electrode cable according to the invention has a stylet channel which is formed by a tube made of a biodegradable, biocompatible polymer material, attached to the exterior of the cable sheath or sleeve, with about the same length as the cable. The tube is preferably being made of thin-walled, soft, biodegradable polymer material. When a material is selected with an appropriate degradation time, e.g. from about 1 hour to days, weeks or even months, a substantially thinner and more flexible electrode, compared to known cables, is obtained after the stylet sleeve has degraded or dissolved. The cable's conductor or conductors can consist of individual straight or twisted wires and fit in the space which would normally have served as a central stylet channel.

DESCRIPTION OF THE DRAWINGS

The single FIGURE shows a schematic perspective view (enlarged) of a small part of an electrode cable constructed in accordance with the present invention.

DESCRIPTION OF THE PREFERRED EMBODIMENTS

The embodiment of electrode cable 10 according to the invention shown in the FIGURE, is a multipolar electrode cable, having four individual, electrically insulated conductors 12, 14, 16 and 18, which are bundled and enclosed in an outer sleeve 20 made of e.g. silicone rubber. More or fewer conductors can be used and extend axially in the longitudinal direction of the cable 10. These conductors extend straight or can be intertwined. Alternatively, the conductors can be helically coiled in the conventional manner, particularly at the distal end section of the electrode cable in order permit the formation there of a J-shaped electrode for fixing in the atrium. A combination of helically coiled and straight or twisted conductors is also possible.

According to the present invention, a thin, soft, tubular element 22, made of biodegradable, biocompatible polymer material extending axially along the entire length of the electrode 10, from a proximal end to a distal end thereof, is attached to the exterior of the sleeve 20. The tubular element 22 forms a channel 24 for a stylet (not shown) which is to be inserted into the channel 24 upon the introduction of the electrode cable 10 into a vein and on to the heart to stiffen the cable 10 to the desired degree and to guide it to the desired fixing site in the heart. Since the tubular element 22 no longer has any purpose after the electrode cable 10 has been implanted, according to the present invention the tubular element is made of a material which is biodegradable or which dissolves, through contact with blood, within an appropriate period of time. The electrode cable accordingly can be slimmer and more flexible than a conventional cable, thereby providing more space for e.g. the implantation of more electrode cables, if desired.

A biodegradable polymer material can e.g. be selected from the groups of proteins/amino acid polymers, polyhydroxycarboxyl acids and/or carbohydrate polymers. The proteins/amino acid 20 polymers group may contain gelatin, collagen, polyserine, polythreonine, polyphenylalanine or the like. The polyhydroxycarboxyl acids group may contain e.g. polylactides and/or polyglycolides. The carbohydrate polymer group may contain dextran, starch, hyaluronic acid, cellulose or the like.

The breakdown or degradation time for the tubular element 22 should exceed at least one hour but can range from one or more days up to several months.

Although modifications and changes may be suggested by those skilled in the art, it is the intention of the inventor to embody within the patent warranted hereon all changes and modifications as reasonably and properly come within the scope of his contribution to the art.

I claim as my invention:

1. An electrode cable for implantation in a body, comprising an insulating sleeve containing at least one elongate, flexible electrical conductor with a distal end and a proximal end, an electrode arranged on the distal end of the conductor adapted for interaction with tissue and a stylet channel for insertion of a stylet, the stylet channel formed by a tube of a biodegradable, biocompatible material, attached to an exterior of the sleeve and having a length substantially equal to a length of the sleeve.

2. An electrode cable according to claim 1, wherein the tube is comprised of a thin-walled, soft, biodegradable polymer material.

3. An electrode cable according to claim 1, wherein said material is a proteins/amino acid polymer selected from the group consisting of gelatin, collagen, polyserine, polythreonine and polyphenylalanine.

4. An electrode cable according to claim 1, wherein said material is a polyhydroxycarboxyl acid selected from the group consisting of polylactides and polyglycolides.

5. An electrode cable according to claim 1, wherein said material is a carbohydrate polymer selected from the group consisting of dextran, starch, 35 hyaluronic acid, and cellulose.

6. An electrode cable according to claim 1, wherein said material is a polymer material having a degradation time exceeding one hour.

* * * * *